US012708481B2

(12) United States Patent
Udale et al.

(10) Patent No.: US 12,708,481 B2
(45) Date of Patent: Aug. 18, 2026

(54) MAGNETIC MARKERS FOR IMAGING AND SURGICAL GUIDANCE

(71) Applicant: ENDOMAGNETICS LTD., Cambridge (GB)

(72) Inventors: Robinson Udale, Cambridgeshire (GB); Gabriel Villar, Cambridgeshire (GB)

(73) Assignee: ENDOMAGNETICS LTD (GB)

( * ) Notice: Subject to any disclaimer, the term of this patent is extended or adjusted under 35 U.S.C. 154(b) by 0 days.

(21) Appl. No.: 18/706,356

(22) PCT Filed: Nov. 3, 2022

(86) PCT No.: PCT/GB2022/052779
§ 371 (c)(1),
(2) Date: Apr. 30, 2024

(87) PCT Pub. No.: WO2023/079292
PCT Pub. Date: May 11, 2023

(65) Prior Publication Data

US 2025/0255693 A1 Aug. 14, 2025

(30) Foreign Application Priority Data

Nov. 3, 2021 (GB) ..................................... 2115827

(51) Int. Cl.
*A61B 90/00* (2016.01)
*A61B 5/06* (2006.01)
(Continued)

(52) U.S. Cl.
CPC ...... *A61B 90/39* (2016.02); *A61B 2090/3954* (2016.02)

(58) Field of Classification Search
CPC . A61B 90/39; A61B 5/062; A61B 2034/2051; A61B 2562/0223; A61B 5/064; A61B 2034/2046
See application file for complete search history.

(56) References Cited

U.S. PATENT DOCUMENTS 5,650,236 A 7/1997 Hirano et al.
5,664,582 A * 9/1997 Szymaitis ................ A61B 5/06 128/897
(Continued)

FOREIGN PATENT DOCUMENTS

EP 3517068 7/2019
GB 2582123 1/2018
(Continued)

OTHER PUBLICATIONS

Sentimag® system of Endomagnetics Ltd https://web.archive.org/web/20210429061527/https://www.endomag.com/sentimag/ (5 pages).
(Continued)

*Primary Examiner* — Scott Luan
(74) *Attorney, Agent, or Firm* — K&L GATES LLP

(57) ABSTRACT

An implantable marker for imaging and surgical guidance by susceptometry comprising one or more pieces of a ferromagnetic material having a total length to diameter ratio of at least about 500, and a total volume of less than about $1\times10^{-11}$ $m^3$. The one or more pieces of ferromagnetic material may have a high initial relative permeability ($\mu_{r,i}$) >about 1000. Also disclosed is a detection system for locating an implantable marker comprising such an implantable marker; at least one drive coil arranged to excite the marker with an alternating magnetic field, and at least one sense coil arranged to detect a signal received from the excited marker; a magnetic field generator arranged to drive an alternating magnetic field through the at least drive coil; and at least one detector arranged to receive the signal from the sense coil and detect one or more harmonics of the drive frequency in the received signal.

25 Claims, 12 Drawing Sheets

(51) Int. Cl.

| | |
|---|---|
| ***A61B 17/00*** | (2006.01) |
| ***A61B 34/20*** | (2016.01) |
| ***G01R 33/16*** | (2006.01) |

(56) References Cited

U.S. PATENT DOCUMENTS

| | | | |
|---|---|---|---|
| 5,921,583 | A | 7/1999 | Matsumoto et al. |
| 6,140,727 | A | 10/2000 | Goto et al. |
| 6,230,038 | B1 | 5/2001 | von Gutfeld et al. |
| 2004/0127787 | A1 | 7/2004 | Dimmer et al. |
| 2015/0264891 | A1 | 9/2015 | Brander et al. |
| 2017/0252124 | A1 | 9/2017 | Greene et al. |
| 2018/0142423 | A1 | 5/2018 | Manov et al. |
| 2019/0223975 | A1 | 7/2019 | Agostinelli et al. |
| 2021/0153970 | A1 | 5/2021 | Agostinelli et al. |

FOREIGN PATENT DOCUMENTS

| | | | |
|---|---|---|---|
| JP | 2020078628 A * | 5/2020 | ............. A61B 90/39 |
| WO | 2006/119645 A1 | 11/2006 | |
| WO | 2011067576 | 6/2011 | |
| WO | 2014013235 | 1/2014 | |
| WO | 2014032235 | 3/2014 | |
| WO | 2014140566 | 9/2014 | |
| WO | 2014140567 | 9/2014 | |
| WO | 2016193753 | 12/2016 | |
| WO | 2019180580 | 9/2019 | |

OTHER PUBLICATIONS

Reig et al., "Role of MRI to Assess Response to Neoadjuvant Therapy for Breast Cancer", Journal of Magnetic Resonance Imaging, Dec. 2020, vol. 52, No. 6, pp. 1587-1606.

Gao et al., "Reduction of artifact of metallic implant in magnetic resonance imaging by combining paramagnetic and diamagnetic materials", Journal of Applied Physics 107, 09B323 (2010), 6 pages.

Chalakuzhiyl et al., "Interactions between magnetic resonance imaging and dental material", Journal of Pharmacy and Bioallied Sciences, Jun. 2013, vol. 5, Supplement 1, pp. S113-S116.

Baylis et al., "Cobalt Essential to High Performance Magnetics", Cobalt Conference—2012 (22 pages).

Graphite Machining and Custom Graphite Parts, Jan. 28, 2021 https://web.archive.org/web/20210128045136/https://www.graphitestore.com/custom-machining (1 page).

Graphite Machining, Products, and Applications, May 8, 2021 https://web.archive.org/web/20210508051413/https://www.semcocarbon.com/capabilities/graphite-machining (2 pages).

Pyrolytic Carbon for Biomedical Applications, Jun. 13, 2002 https://www.azom.com/article.aspx?ArticleID=1463 (3 pages).

Von Gutfeld et al., "Amorphous magnetic wires for medical locator applications", Applied Physics Letters, vol. 81, No. 10, Sep. 2, 2002 (3 pages).

EUIPO—eSearch, EM007693270, Feb. 21, 2020, RCD file information (3 pages).

Magseed® marker of Endomagnetics Ltd https://web.archive.org/web/20200501160132/https://www.endomag.com/magseed/overview/ (5 pages).

Hargreaves et al., "Metal Induced Artifacts in MRI", AJR Am J Roentgenol, Sep. 2011; 197(3):547-555, pp. 1-20.

Masood, "Neoadjuvant chemotherapy in breast cancers", Women's Health 2016, vol. 12(5) 480-491.

Koh et al., "Introduction of a New Staging System of Breast Cancer for Radiologists: An Emphasis on the Prognostic Stage", Korean Journal of Radiology 2019; 20(1): 69-82.

Combined UK Search and Examination Report for Application No. GB2115827.4 dated Mar. 16, 2022 (6 pages).

International Search Report and Written Opinion for International application No. PCT/GB2022/052770 mailed on Feb. 8, 2023 (15 pages).

Varga et al., "Magnetically Bistable Microwires: Properties and Applications for Magnetic Field, Temperature, and Stress Sensing", Chapter 8, pp. 169-212.

Sulla et al., "Utilizing Magnetic Microwires for Sensing in Biological Applications", Journal of Electrical Engineering, vol. 66 No. 7/s, 2015, pp. 161-163.

Baranov, "Cast Amorphous Magnetic Microwires for Medical Locator Applications", 2nd International Conference on Nanotechnologies and Biomedical Engineering, Chisinau, Republic of Moldova, Apr. 18-20, 2013, pp. 589-592.

Zhukov, Extracts from High performance Soft Magnetic Materials, Springer Series in Material Science, vol. 252 (2017), 60 pages.

Thiruchelvam et al., "Abstract nr P3-01-17: Mri study of a novel paramagnetic seed for clinically occult breast tumor localization", Cancer Research (2022) 82 (4_Supplement): P3-01-17 (2 pages).

Shinichiro Ito, "Fundamentals of Ferrite for Noise Suppression", TDK EMC Technology—EMC Design Guidebook, [online], Sep. 3, 2021, https://product.tdk.com/system/files/dam/doc/content/emc-guidebook/ja/jemc_basic_06. pdf, (18 pages).

* cited by examiner

| | | | | Helix | Helix | | | | Helix | Helix |
|---|---|---|---|---|---|---|---|---|---|---|
| Geometry | $L$ = 5mm | $L$ = 5mm $s$ = 1mm | $D$ = 5mm | $D$ = 5mm $p$ = 1mm $N$ = 5 | | $L$ = 1mm | $L$ = 1mm $s$ = 1mm | $D$ = 1mm | $D$ = 1mm $p$ = 1mm $N$ = 5 | |
| $\frac{m_z}{m_{thresh}}$ | 4.7 | 8.8 | 11 | 87 | 3.2 | 0.12 | 0.25 | 0.36 | 2.4 | 8.2 |
| $\frac{m_z}{V}$ (a.u.) | 54 | 51 | 42 | 64 | 2.3 | 7.1 | 7.1 | 6.6 | 8.3 | 29 |
| Dimensions covered | 1 | 1 | 2 | 2.0 | | 1 | 1 | 2 | 1.3 | |
| $\frac{m_z}{V}$ for 3D (a.u.) | 18 | 17 | 28 | 43 | | 2.4 | 2.4 | 4.4 | 13 | |

*mz* means the magnetic dipole moment of the wire in the direction of the magnetic field.
*mthresh* is a threshold value for that magnetic dipole moment required for sensing at 25mm. It is a constant in this figure.
*V* is the volume of the wire.
"Dimensions covered" and "*mz/V* for 3D" are measures of isotropy.

FIG. 6

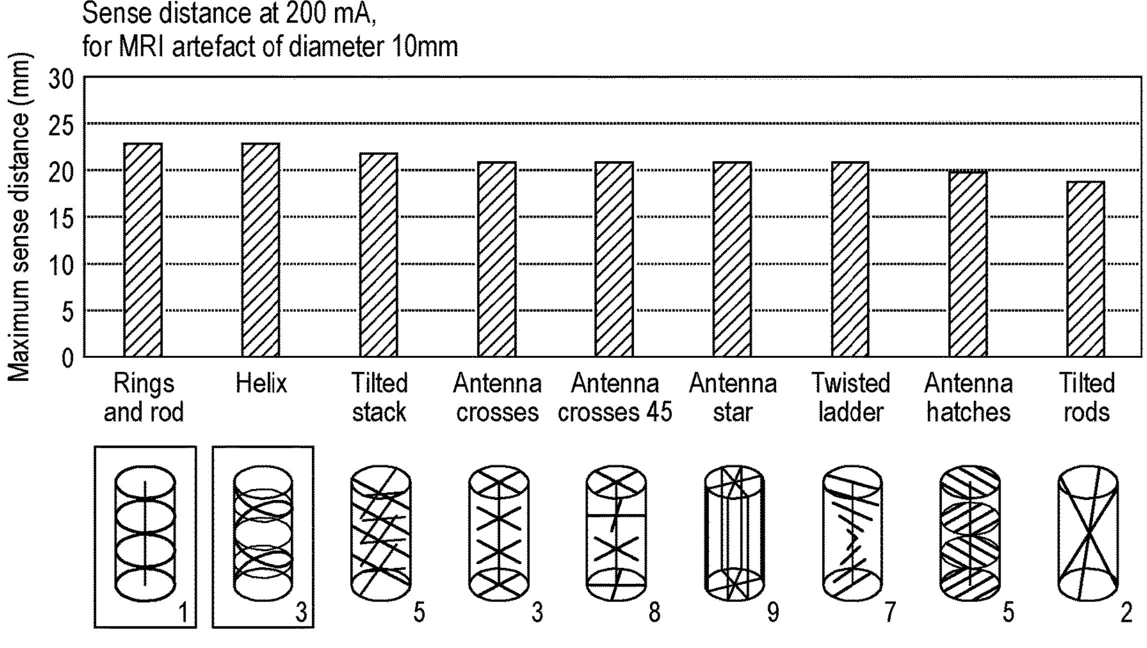

Material parameters: $\mu_r$ = 72,000, $B_S$ = 0.55T, Wire Ø 30 μm
Max Total length 21 mm

FIG. 7

MAGNETIC MARKERS FOR IMAGING AND SURGICAL GUIDANCE

CROSS REFERENCE TO RELATED APPLICATIONS

This is the national phase under 35 U.S.C. § 371 of International Application No. PCT/GB2022/052779 filed on Nov. 3, 2022, which claims priority to and the benefit of United Kingdom Patent Application No. 2115827.4 filed on Nov. 3, 2021, the entire disclosures of which are incorporated by reference herein.

FIELD OF THE DISCLOSURE

This disclosure relates in general to the field of magnetic markers for imaging and surgical guidance, in particular to magnetic susceptometry markers with a reduced MRI artefact.

BACKGROUND

Markers are used to guide surgeons to a region of interest during a surgical procedure, where the site of interest is not physically visible or palpable, for example a small tumour that needs to be excised. Ideally, such a marker will be deployable through a narrow gauge needle e.g. 18G to 12G in order to reduce trauma to the patient. Typically, such markers are less than 10 mm in length so as to be unobtrusive and to minimise trauma. The marker may be placed during a biopsy or other surgical procedure at a site of interest in the body, for example a cancer lesion. The marker is placed under imaging guidance such as ultrasound or X-ray/mammography. During subsequent surgery, the marker is detected and localised using a handheld probe which provides audible, visual or other feedback to the surgeon to guide the surgery. Typically, the marker is excised along with the surrounding tissue.

One such approach is to use a marker containing a radioisotope such as Iodine 125 which can be detected using a handheld gamma detection probe. However, use of radioactive materials is closely regulated, making it challenging to set up a radioactive seed programme in all but the largest academic hospital centres.

A further approach is discussed in the Applicant's earlier published patent applications (for example, WO 2011/067576, WO 2014/032235 and WO 2014/140567) and uses magnetic fields and a magnetic marker with high magnetic susceptibility. A handheld susceptometry probe generates an alternating field which excites a magnetically responsive marker, and detects the responding magnetic field. This approach has been found to be highly effective for deeper sensing. However, the systems suffer from the drawback that an artefact is created in a MRI setting that is large compared to the marker itself.

MRI is used to image lesions not visible on ultrasound or mammography for invasive breast cancer and MRI monitoring is increasingly being used for evaluation of neoadjuvant therapy prior to surgical excision, allowing for the size for the tumours to be tracked after neoadjuvant therapy and prior to surgery. A MRI artefact should not compromise the assessment by the healthcare professional of the size of the tumour where the marker has been placed, as explained in further detail below.

Ferromagnetic materials are well known for creating MRI distortions and have been widely described in the scientific literature. For example, Hargreaves et al. (Metal Induced Artifacts in MRI, August 2017, DOI: 10.2214/AJR.11.7364) explains that some ferromagnetic materials may be safe for MRI but would still create significant artefacts. The artefact is predominantly generated by the component of the magnetic field generated by the ferromagnetic object ($B_y$) that is in the same direction as the main field produced by the MRI machine. The effect of $B_y$ is to shift the local Larmor frequency of protons near the object, and if that shift is large enough, those protons will not appear in the correct slice reconstructed by the MRI machine.

Therefore, the Applicant has identified a need for a small ferromagnetic marker for detection by susceptometry with acceptable isotropy of response, long sense distance and showing a small MRI artefact. The MRI artefact of such a marker should not compromise the assessment by the healthcare professional of the size of the tumour, as monitoring a decrease in the size of the tumour would offer positive options in the management of a cancer patient. In this respect, breast cancer stages are evaluated using several criteria such as the tumour size, whether the tumour has spread to the lymph nodes and if the cancer has spread to other parts of the body (metastasis). Early stage cancers where breast conserving surgery using lumpectomy can be envisaged should preferably present a tumour size of 2 cm of less. Shashla (Neoadjuvant chemotherapy in breast cancers, September 2016, DOI: 10.1177/1745505716677139) indicates that smaller tumour size represents a good prognostic factor, and residual tumours of >2 cm are associated with higher rates of locoregional tumour recurrence after neoadjuvant chemotherapy. Koh et al. (Introduction of a New Staging System of Breast Cancer for Radiologists: An Emphasis on the Prognostic Stage, January 2019, DOI: 10.3348/kjr.2018.0231) indicate that tumours where the size is below 2 cm are classified as T1 and correspond to a cancer stage 1 or 2 which is typically when a breast conservation surgery can be envisaged. A larger tumour will more likely lead to more radical procedures, such as mastectomy.

Therefore, it is desirable to be able to size the tumour under MRI when it exceeds 2 cm in diameter, enabling assessment to observe whether the tumour has shrunk to a level that would allow breast conservation surgery. According to the present disclosure, a marker providing an artefact of approximately 2 cm will still allow sufficient radio diagnostics to determine if the tumour is bigger than 2 cm and may require further neoadjuvant treatment.

It is an aim of the present disclosure provide an improved magnetic marker with a reduced MRI artefact that overcomes, or at least alleviates, the above-mentioned drawbacks.

SUMMARY OF THE DISCLOSURE

According to a first aspect of the present disclosure there is provided an implantable marker for imaging and surgical guidance, the marker comprising one or more pieces of a ferromagnetic material having a total length to diameter ratio of at least 50 and a total volume of less than $1\times10^{-10}$ $m^3$.

In a particular aspect of the disclosure, the ferromagnetic material may have a total length to diameter ratio of at least about 500.

Suitably, the ferromagnetic material may have a total volume of less than about $1\times10^{-11}$ $m^3$; preferably less than about $6\times10^{-12}$ $m^3$.

Suitably, the one or more pieces of ferromagnetic material may have a high initial relative permeability ($\mu_{r,i}$)>about 1000; preferably at least about 2000.

Where the term "length" is used, unless explicitly stated otherwise, the skilled person will appreciate that this means the length of a non-linear marker shape as if the marker were extended in a linear manner. For example, if the marker is a helix, the length means the length of the marker if straightened and extended in a linear manner. Where the marker comprises a plurality of pieces of ferromagnetic material, the length may comprise the combined length of the plurality of pieces.

In some embodiments, the one or more pieces of ferromagnetic material may have circular cross-section with a readily measurable diameter. In some embodiments, the one or more pieces of ferromagnetic material may have a non-circular cross-section; for instance, one or more pieces of ferromagnetic material may comprise strips having a generally rectangular cross-sectional shape. Thus, by "diameter" herein is also meant width (e.g. maximum width) in the case of a non-circular piece of ferromagnetic material. Alternatively, the length to diameter ratio may equate to the ratio of length to the square root of the cross-sectional area of the piece.

It has been found that a marker with a high length to diameter ratio as defined herein and a low volume balances the provision of a good sensing response with a small MRI artefact. Increasing the length to diameter ratio of the at least one piece of ferromagnetic material improves the sensing response of the marker. Reducing the volume of the ferromagnetic material reduces the MRI artefact created by the marker.

The marker may be detectable by magnetic susceptometry probes such as the one described in WO 2014/140566 A1. The magnetic susceptometry probes may produce a magnetic field strength between about 0.1 mT and about 2.0 mT at source; preferably about 0.2 mT and about 1.2 mT, giving rise to a field strength of between about 0.04 mT and about 0.4 mT within about 5 mm of the probe. Suitably, this may allow the marker of the present disclosure to be detected at a range of up to about 50 mm, 60 mm, 70 mm or 80 mm from the probe. The precise detection range for a particular marker depends to an extent on its configuration, as described herein.

The total length to diameter ratio of the one or more pieces of ferromagnetic material may be at least about 100, at least about 200, at least about 300, at least about 400, or at least about 500. In some embodiments, the total length to diameter ratio of the one of more pieces of ferromagnetic material may be at least about 650, at least about 700, at least about 750, at least about 1000, at least about 1500, at least about 2000, at least about 2500, at least about 3000 or more. In some embodiments, the total length to diameter ratio of the one or more pieces of ferromagnetic material may be about 2400.

The total volume of the one or more pieces of ferromagnetic material may be less than $5\times10^{-11}$ m$^3$, $3\times10^{-11}$ m$^3$, or $1\times10^{-11}$ m$^3$. In some embodiments, the total volume of the one or more pieces of ferromagnetic material may as low as $1\times10^{-12}$ m$^3$.

By way of example, the one or more pieces of ferromagnetic material may have a total length of 50 mm and a diameter of 15 μm. In such an example, the total length to diameter ratio of the one or more pieces of ferromagnetic material may be approximately 3333, and the volume may be approximately $9\times10^{-12}$ m$^3$.

In another example, the one or more pieces of ferromagnetic material may have a total length of 36 mm and a diameter of 15 μm. In such an example, the total length to diameter ratio of the one or more pieces of ferromagnetic material may be approximately 2400, and the volume of ferromagnetic material may be approximately $6.4\times10^{-12}$ m$^3$.

In a preferred embodiment, the marker may comprise a wire or strip of ferromagnetic material having a length of at least 3 mm, 6 mm, 10 mm, 20 mm, 30 mm, 35 mm, 50 mm, or 100 mm long. A wire may have a diameter less than 100 μm, or less than or equal to 50 μm, 30 μm, 15 μm, or 10 μm. The marker may comprise a wire or strip of ferromagnetic material having a length of no more than 3 mm, 6 mm, 10 mm, 20 mm, 30 mm, 35 mm, 40 mm, 50 mm, or 100 mm long. Suitably, the wire or strip may be formed into one or more pieces, as described herein.

The marker according to the present disclosure may provide an MRI artefact of less than 3 cm in diameter, more preferably less than 2.5 cm, especially less than 2 cm. The size of the MRI artefact may vary depending on the strength of the MRI field, and the size of the MRI artefact may be detected in a 1.5T, or 3.0T MRI scanner, or any other suitable MRI scanner.

The ferromagnetic material may have a low saturation induction, for example less than or equal to 1T. Provision of a ferromagnetic material with a low saturation induction may limit the size of the MRI artefact created by the material when the marker is subjected to an MRI magnetic field strength which is greater than the field strength needed to saturate the magnetisation of the ferromagnetic material.

The ferromagnetic material may have a high initial relative permeability, for example, $(\mu_{r,i})>1000$. Suitably, the ferromagnetic material may have a high initial relative permeability of more than 10,000. Provision of a ferromagnetic material with a high initial relative permeability may improve the sensing performance of the marker.

Preferred materials that possess the required characteristics for markers according to the present disclosure are particular metals and amorphous metals. Suitably, the ferromagnetic material may be ductile such that it can be formed into a wire. The ferromagnetic material may be pliable so that the at least one piece may be formed into a desired configuration; for example to decrease or minimise a magnetic isotropy ratio of the marker, as described below. Preferably cobalt or nickel-based ferromagnetic alloys, especially those sold under the trade names Yshield™ and Metglas 2714A™, may be used.

The ferromagnetic material is preferably in the form of a wire, for example cylindrical wire with a circular cross-section, flat wires or strips and the marker may comprise one or more pieces of the material configured to provide maximum sense performance, a high isotropy of sense performance and a reduced MRI artefact. As used herein, the term "wire" includes strips as well as wires, unless the context indicates otherwise.

Preferred embodiments of markers according to the present disclosure may include one or multiple wires or strips according to the first aspect of the disclosure provided as rods, coils and/or rings or a combination of the aforesaid rods, coils and/or rings. The one or more multiple wires or strips may be configured to define a tortuous path or paths, either individually or in combination, extending in several different directions and/or including twists, bends, or turns in order to decrease the magnetic anisotropy ratio of the marker. An embodiment of markers according to the present disclosure may include a helical coil with 1, 2, 3, 4, 5, 6 or more coils. Where the ferromagnetic material is provided in the form of a multiple helix, for example a triple or quadruple helix, the individual helices are preferably non-touching with each other.

The or each helical coil may have a pitch to diameter ratio of 1.2, 1.3, 1.4, 1.5, 1.6, 1.7, or more. In some embodiments, the helical coil may have a pitch to diameter ratio of 1.33.

As used herein, the "magnetic anisotropy ratio" is the ratio of the strongest to weakest magnetic signals produced by the marker at a constant distance at different orientations of the marker relative to a probe. Since the calculated distance between the marker and the probe depends relatively weakly on the magnetic sense response, the marker may suitably have anisotropy ratio of less than 7 (i.e. between 1 and 7), preferably less than 5, and more preferably less than 3.

Particularly preferred arrangements of the one or more wires are shown in FIG. 7 of the accompanying drawings.

The ferromagnetic material configured into the required shape may be encapsulated in a cylindrical housing. The cylindrical housing is preferably injectable in order to allow for placement of the marker. Suitably, therefore, the housing may have a maximum diameter such that it is deployable through a narrow gauge needle e.g. 18G to 12G. The marker may be packaged within other materials, or a coating may be applied to the marker, to ensure that the marker is biocompatible and robust. The marker may be encased in a tube, for example made from Nitinol, titanium, stainless steel or other biocompatible alloys, the material preferably being non-magnetic and having a relatively low conductivity. A low conductivity may comprise a conductivity of below 106 Siemens. Suitable coating materials include a polymer coating, such as Invar, FEP, Parylene, PTFE, ETFE, PE, PET, PVC or silicone or an epoxy based encapsulant.

The arrangement of wires may extend in a plurality of directions and/or across a plurality of planes. For example, the arrangement of wires may comprise two, three, four, or more linear wires, the wires extending in different directions in the same or different planes. In another example, the arrangement of wires may comprise two, three, four, or more curved or bent wires, the curved or bent wires extending in a single plane, for example a ring shaped wire, an L-shaped wire, or across a series of planes, for example a helical wire. The arrangement of wires may comprise at least one linear wire and at least one curved or bent wire. The linear wire and curved or bent wire may extend in different planes, for example mutually orthogonal planes.

In one embodiment, the arrangement of wires or strips within the housing are provided as offset parallel rods, substantially perpendicular rods and/or rods placed end on end, preferably being separated from each by at least one diameter length of the rod. More preferably, two or more rods may be crossed at angles to each other; for example two rods may be crossed substantially at right angles to each other. The marker may include a stacked arrangement of multiple such crossed rods. The stacked cross arrangement may have the crosses in line or rotated with respect to each other, for example, each cross being rotated substantially by 45 degrees to an adjacent stacked cross. In some embodiments, each cross may be disposed in a respective plane which is substantially orthogonal to an axis defined by the housing; for example a longitudinal axis of a cylindrical housing of the kind described above. In some embodiments, each cross may be disposed in a respective plane which is tilted relative to such an axis defined by the housing. The planes may suitably be spaced apart along the axis. The crosses may thus be disposed in two or more respective parallel planes which are orthogonal to or tilted with respect to the housing axis.

Alternative configurations of rods may be provided, such, for example, as one or more groups of parallel rods which are provided throughout the housing. The rods in each group may extend in a respective plane, which may be tilted or substantially orthogonal with respect to an axis defined by the housing; for example a longitudinal axis of a cylindrical housing. Thus, the groups of parallel rods may be arranged in a series of respective planes which are spaced apart along the longitudinal axis of the housing. As before, the planes may be spaced apart along the axis. The rods in each group may be aligned with and/or rotated with respect to the rods in at least one other group.

In some embodiments, each group of parallel rods may be rotated by about 15-90° with respect to each other group; for example, four groups of parallel rods may be arranged such that each group is rotated by about 45°, about 60° and about 90° with respect to each respective one of the other groups. In another configuration, said tilted rods may form a twisted ladder configuration in which each rod extends in a respective plane that is substantially orthogonal to an axis defined by the housing, particularly a longitudinal axis, the planes being spaced apart along the axis, and is rotated through an angle of about 10-45° with respect to its adjacent rod or rods; for example, the arrangement may comprise 8 linear rods, each of which is rotated by about 11.25° with respect to each of its neighbouring rod or rods.

Optionally, one or more longitudinal rods may be provided through the housing for example, through the centre thereof or independently of the cylinder casing, forming shapes such as the ones providing the same rods orientations described in GB 2582123 A (such as the three or four edges tetrahedron, the lone circle linked to a perpendicular rod, the "Jack" shape or the snake), the contents of which are incorporated herein by reference; e.g. as shown in FIGS. 11 to 19. In some embodiments, one or more transverse rods may be provided through the housing, extending in one or more planes which are substantially orthogonal to an axis of the housing, for example a longitudinal axis of a cylindrical housing.

In a more preferred embodiment, the markers according to the first aspect of the disclosure are provided in a helix shape or comprising multiple spaced apart rings, optionally including one or more straight longitudinal rods extending through the helix or rings.

In a preferred embodiment, the marker is provided as a single helix combined with one longitudinal wire aligned parallel to a longitudinal axis of the helix, or as a multiple helix, e.g. a double, triple or quadruple helix. Preferably, the pitch of the or each helical coil may be about 1.0-1.5 times the diameter of the coil.

According to another aspect of the present disclosure, there is provide a detection system for locating an implantable marker, the system comprising: an implantable marker according to the first aspect of the disclosure, at least one drive coil arranged to excite the marker with an alternating magnetic field and at least one sense coil arranged to detect a signal received from the excited marker; a magnetic field generator arranged to drive an alternating magnetic field through the at least drive coil; and at least one detector arranged to receive the signal from the sense coil and detect one or more harmonics of the drive frequency in the received signal.

BRIEF DESCRIPTION OF THE DRAWINGS

Following is a detailed description by way of example only with reference to the accompanying drawings of embodiments of the present disclosure:

In the drawings:

FIG. 6 details sense response for different embodiments of a marker according to the disclosure, illustrating their geometry, dimensions covered and their effect on MRI artefacts;

FIG. 7 shows maximum sense distance for different embodiments of a marker according to the disclosure, having good sensitivity and low MRI artefact;

DEFINITIONS

Figure 1A:
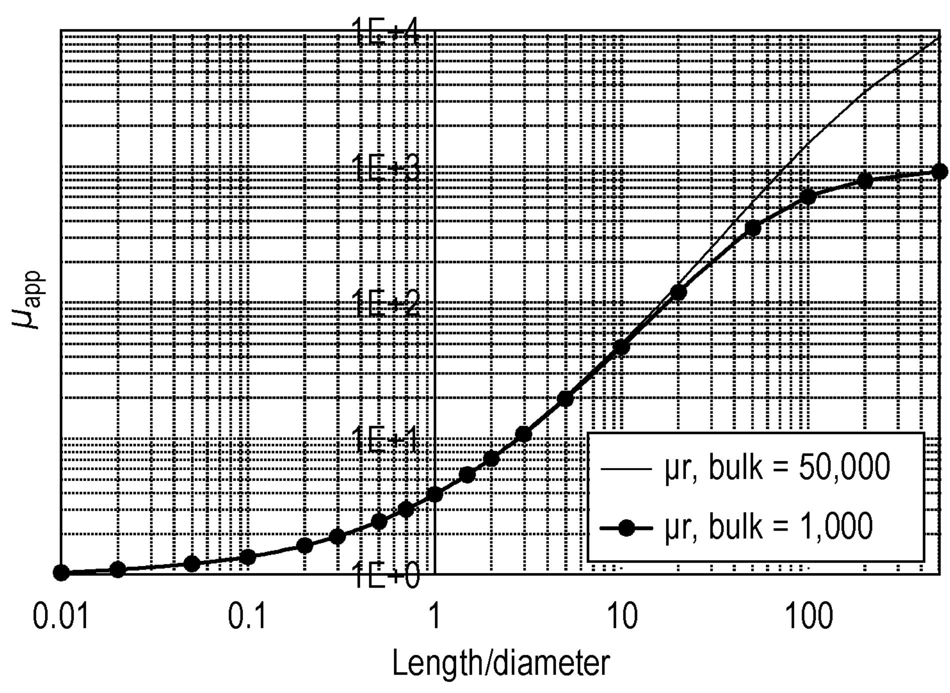
FIG. 1*a* is a graph illustrating the effective permeability ($\mu_{app}$) of a ferromagnetic material vs shape and material.

Unless defined otherwise, all technical and scientific terms used herein generally have the same meaning as commonly understood by one of ordinary skill in the art.

Magnetic flux density (B) is a vector quantity measuring the strength and direction of the magnetic field around a magnet or an electric current.

Magnetic field strength, also known as magnetizing field (H) is a vector field that describes the magnetic influence of an external magnetic field on moving electric charges, electric currents, and magnetic materials.

Coercivity is the magnetizing field (H) needed to demagnetize a ferromagnetic material completely.

Hard magnetic materials have a high coercivity. They are also referred as permanent magnets.

Soft magnetic materials have low coercivity. They are easily magnetised and demagnetised.

Magnetisation, also known as magnetic polarisation (M) is a vector field that expresses the density of permanent or induced magnetic dipole moments in a magnetic material.

Saturation of induction is the state reached when an increase in applied external magnetic field H cannot increase the magnetization M of the material further. In this state, the total magnetic flux density that results is called the saturation induction ($B_s$), and the magnetisation is the saturation magnetisation ($M_s$).

Initial susceptibility ($\chi$) is a measure of how much a material of infinite extent will become magnetised in a small applied magnetic field. It is defined as $\chi$=M/H for small H, or equivalently $$\chi = \frac{dM}{dH}\bigg|_{H=0}.$$

Apparent initial susceptibility ($\chi_{app}$), also known as effective susceptibility, is the initial susceptibility for a material of specific geometry in a small applied magnetic field. That is, it is $\chi$ after taking into account the demagnetisation factor (see below).

Magnetic permeability (μ) is the measure of a material's resistance against the formation of a magnetic field, where $\mu=B/H$.

Relative magnetic permeability ($\mu_r$) is the ratio of magnetic permeability to the permeability of free space ($\mu_0$), that is $\mu_r=\mu/\mu_0$.

A ferromagnetic material has a variable relative permeability ($\mu_r$) that increases relative to the magnetic field and up to a maximum. Many ferromagnetic materials have a maximum relative permeability that can exceed 100,000.

A paramagnetic material has a constant relative magnetic permeability ($\mu_r$) which is slightly more than 1.

A diamagnetic material has a constant relative magnetic permeability ($\mu_r$) slightly lesser than 1. Diamagnetism causes a repulsive effect by creating a small magnetic field in opposition to an externally applied field.

Initial relative magnetic permeability ($\mu_{r,i}$) is the value of $\mu_r$ for small H, and is related to the initial susceptibility by $\mu_r=1+\chi$.

Apparent relative magnetic permeability ($\mu_{app}$) is the relative magnetic permeability of a material of specific geometry. That is, it is $\mu_r$ after taking into account the demagnetisation factor.

Demagnetising field, also known as stray field is the magnetic field (H) generated by the magnetisation (M). It gives rise to shape anisotropy in ferromagnets with a single magnetic domain, and to magnetic domains in larger ferromagnets.

Demagnetisation factor is a number that describes the strength of the magnetic field produced by an object of specific geometry, compared to an object of infinite extent. It must be used in order to determine the demagnetising field. An arbitrarily shaped magnetic object has a total magnetic field that varies with location inside the object and can be quite difficult to calculate. This makes it very difficult to determine the magnetic properties of a material such as, for instance, how the magnetisation of a material vanes with its shape and with the magnetic field.

Magnetic anisotropy describes the variation of magnetic properties depending on the material orientation, relative to an externally applied magnetic field.

The magnetic moment, also known as magnetic dipole moment, is a vector quantity that describes the magnetic strength and orientation of a magnet or other object, such as an electric current loop, that produces a magnetic field H.

MRI metal artefacts are distortions of the MR image characterised by a region of signal void (black) or bright fringing in the vicinity of a metal object. They occur at interfaces of tissues and metal with different magnetic susceptibilities, which cause local magnetic fields to distort the external magnetic field. This distortion changes the precession frequency in the tissue leading to spatial mis-mapping of information.

DETAILED DESCRIPTION

The present disclosure relates to an improved magnetic marker that allows for surgical guidance and provides a small enough MRI artefact (preferably less than 2 cm) so as to allow effective radio diagnostics. It has been surprisingly found that using thin wires of ferromagnetic material as defined herein, having a high length to diameter ratio (as defined above) of greater than 50, preferably at least about 500, more preferably at least 650, at least 750 or at least 1000, and low volume of less than about $1\times10^{-10}$ m$^3$, a marker is created that provides a satisfactory sensing performance, balanced with a small MRI artefact. The markers of the present disclosure may be further improved by selecting ferromagnetic material with a low saturation induction which may further limit the MRI artefact size. The markers of the present disclosure may be further improved by selecting a ferromagnetic material with a high initial permeability which may improve sensing performance. Various shapes for such markers, which provide an improved isotropy of magnetic susceptibility, have also been developed.

'Artefacts' can be produced on an MRI image when an object changes the magnetic fields in an MRI machine. Thus, a marker of a ferromagnetic material will produce a significant artefact, reducing their appeal for use as a long-term marker for patients undergoing treatment such as neoadjuvant therapies prior to surgical excision. The artefact is predominantly generated by the component of the magnetic field generated by the ferromagnetic object ($B_y$) that is in the same direction as the main field produced by the MRI machine (here referred to as the y-axis). The effect of $B_y$ is to shift the local Larmor frequency of protons near the object, and if that shift is large enough, those protons will not appear in the correct slice reconstructed by the MRI machine. That is, points at which $|B_y|\geq B_{crit}$ do not appear in the expected slice, where $B_{crit}$ is the magnitude of the y-component of the magnetic flux density B at which a voxel is mapped to a different slice, and the value of which depends on MRI scanning parameters.

At distances large compared to the object, the field produced by a ferromagnetic object can be described by the dipole model. Along the axis of magnetisation, under that model the magnetic flux density is given by $$B = \frac{\mu_0 m}{2\pi y^3},$$

where m is the magnetic dipole moment of the ferromagnetic material and y is the distance from the object to the point of interest. In an MRI machine a ferromagnetic object will typically be saturated, so its magnetic dipole moment is given by $$m = M_s V = \frac{B_s}{\mu_0} V.$$

Combining the equations gives $$B_{MRI} = \frac{B_s V}{2\pi y^3},$$

where $B_{marker,MRI}$ is the field produced by the ferromagnetic material when in an MRI field. That is, if B is the total field and $B_0$ is the field applied by the MRI machine, then $B=B_0+B_{marker,MRI}$. Therefore, it has been found that the strength of the magnetic field from the ferromagnetic object in an MRI machine is dependent on the volume of ferromagnetic material, its saturation induction and the distance away from it.

If we now consider the edge of an MRI artefact, then at that point $B_{marker,MRI}=B_{crit}$, and y describes the distance from the centre of the artefact to its edge. At that point, using the equation above, we obtain $$y^3 = \frac{B_s V}{B_{crit} 2\pi}, \text{ and so } y = \left(\frac{B_s}{B_{crit}} \cdot \frac{V}{2\pi}\right)^{\frac{1}{3}}.$$

If we define the "diameter" of an artefact along the y-axis (although it may not be circular) as a measure of its extent as $D_{artefact,y}=2y$, then it follows that $$D_{artefact,y} = 2\left(\frac{B_s}{B_{crit}} \cdot \frac{V}{2\pi}\right)^{\frac{1}{3}}.$$

In summary, the saturation induction ($B_s$) and volume of magnetic material (V) determine the size of the MRI artefact, as follows:

$$D_{artefact,y} = 2\left(\frac{B_s}{B_{crit}} \cdot \frac{V}{2\pi}\right)^{\frac{1}{3}}$$

This constraint on the maximum volume of magnetic material that you can use makes it difficult to make a marker from a magnetic material that has an effective sense distance, good isotropy and a small artefact. The markers of the present disclosure address this problem.

To apply this finding to a ferromagnetic material that would retain a good magnitude of magnetic field under sensing, the susceptibility in relation to the shape has also been studied.

As above, the magnitude of the magnetic flux density, B, from a ferromagnetic object along the axis of magnetization is given by $$B = \frac{\mu_0 m}{2\pi y^3}.$$

In a magnetic field much weaker than that produced by an MRI machine, such as that produced by magnetic susceptometry probes such as the one described in WO 2014/140566 A1, the magnetisation of the material is $M=\chi_{app}H$, where $\chi_{app}$ is the apparent initial susceptibility. By definition, its magnetic dipole moment, m=MV, so that $m=\chi_{app}HV$, and this in turn gives the following expression for the magnetic field produced by an object when stimulated by a weak field:

$$B = \frac{\mu_0 \chi_{app} H V}{2\pi y^3}$$

Figure 1B:
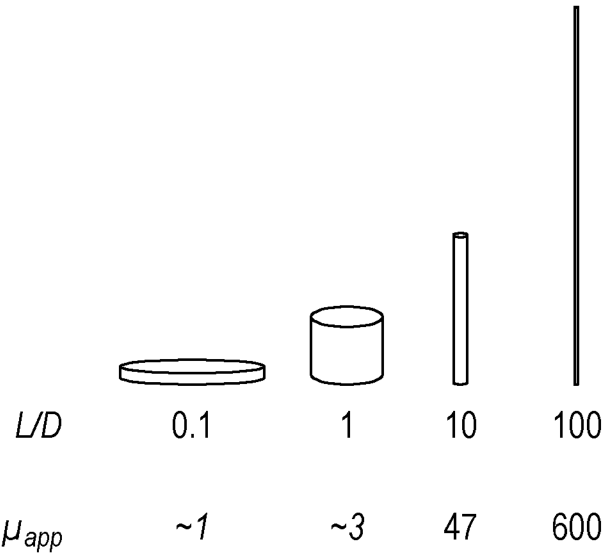
FIG. 1*b* illustrates the shapes of cylinders having different length/diameter ratios.

This last equation demonstrates that the strength of the sense response will be proportional to the (a) the volume of magnetic material (V); (b) the strength of the applied field (H); and (c) the apparent susceptibility of the magnetic material ($\chi_{app}$). This last quantity will be much larger for a long, thin magnetic material as illustrated in FIG. 1 of the accompanying drawings. The equation also shows that the strength of the sense response will reduce with distance away from the marker (in inverse proportion to the distance cubed).

Certain shapes of markers comprising ferromagnetic material have been found to be unsuitable for purpose. For example, a sphere cannot give the expected artefact size for the needed sense distance as the susceptibility will be low for any diameter. It has been found that for an MRI artefact with a diameter below 10 mm under a 1.5T MRI field, the diameter of the sphere cannot exceed 0.18 mm which would be too small to handle during manufacturing and to be seen by the surgeon after extraction of the tumour. On the other hand, to sense beyond 40 mm, the sphere would need to exceed 1.1 mm which would give an artefact much bigger that what would be considered acceptable.

Example 1: Physical Properties of a Marker According to the Disclosure

As mentioned above, during sensing a marker is subjected to a small, oscillating field. Its magnetic response is described by its permeability, $\mu_r$ or susceptibility, $\chi$ (where $\mu_r=1+\chi$). If the initial susceptibility or the initial relative permeability is known, it is possible to predict the magnetic response of the marker. It has been determined that the apparent initial susceptibility depends on the material, its shape and the frequency of the applied field.

It was deduced that increasing a magnetic material's aspect ratio (L/D, where L is the length of a cylinder of the material and D is its diameter) dramatically increases its sense performance in the direction of its central axis. This is illustrated by FIG. 1: as the ratio L/D increases, so does the apparent permeability $\mu_{app}$ of the object, which in turn increases the distance at which it can be sensed. This phenomenon is due to the demagnetisation effect, which may be understood intuitively as follows: if an object is substantially perpendicular to an applied magnetic field, the microscopic magnetic dipole fields produced in the object will mostly act to cancel each other out. Conversely, if the object is substantially parallel to the applied magnetic field (as for a long, thin rod aligned with the field), the microscopic dipoles produced in the object will interact constructively, thereby creating a stronger magnetic field, which in turn allows the marker to be detected more easily.

Under an AC magnetic field, an additional phenomenon takes place: eddy currents induced in the material then create an additional magnetic field that partially shields the material from the external field, thus reducing the sense performance. Eddy currents can make a significant difference when the object subjected to the field has a large area perpendicular to the field. In contrast, for very thin rods (Ø~50 μm), eddy currents actually do not significantly affect the sense performance of magnetic wires. For significantly thicker rods (Ø~500 μm), eddy currents are significant if L/D>1. Therefore, in order to reduce or remove the effect of eddy currents on the sense performance of a magnetic wire, it is preferably that the wire is thin.

For cylinders, aspect ratio is the most important factor.

For rods of aspect ratio L/D<10, initial relative permeability ($\mu_{r,i}$) makes little difference as long as it is >1,000, as evident from FIG. 1. However, for rods of greater aspect ratio, a higher initial relative permeability is beneficial: for example, for a rod of L/D=400, increasing $\mu_{r,i}$ from 1,000 to 50,000 increases $\mu_{app}$ approximately 7-fold.

The magnitude of the ferromagnetic material's magnetic field induced under MRI determines the size of the MRI artefact. During MRI, the marker is subjected to a large, constant field and magnetization saturates at $B_s=\mu_0 M_s$ (the "saturation induction"). The range of $B_s$ for most ferromagnetic materials is ~0.25-1.5 T. Thus, the MRI field (1.5-3.0 T) is strong enough to saturate these materials so the magnetisation of a ferromagnetic marker in MRI can be calculated simply as $M_s B_s=B_s/\mu_0$. So, to minimize the artefact size, a material with a low $B_s$ is required.

Figure 2:
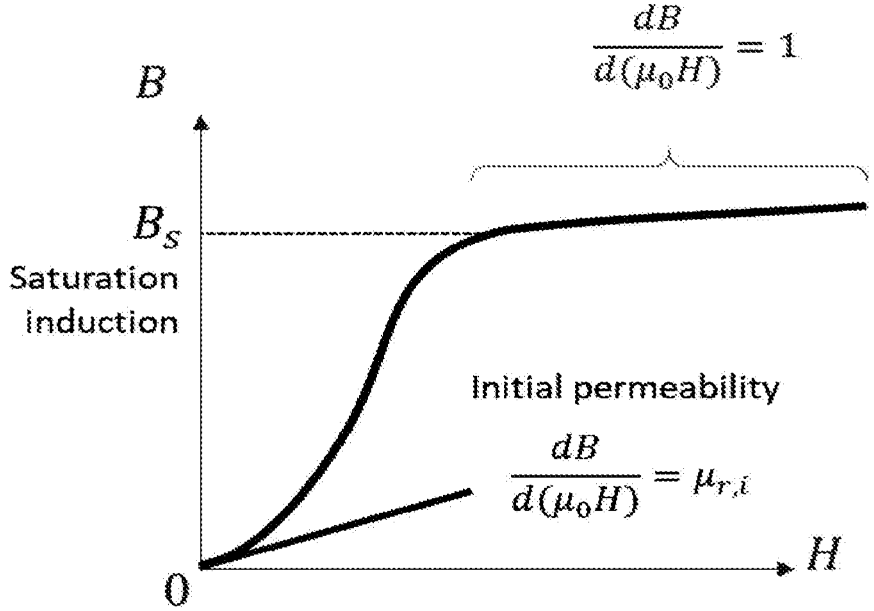
FIG. 2 is a graph of magnetic flux density (B) against magnetic field strength (H) for a ferromagnetic material and an illustration of the definition of the saturation induction ($B_s$) and initial relative permeability ($\mu_{r,i}$).

This is illustrated in FIG. 2 of the accompanying drawings.

This leads to a limited range of properties that need to be met by a marker to provide a satisfactory sensing response and a reduced MRI artefact. A minimal volume of magnetic material should be used, the aspect ratio should be high, and preferably the marker should have a high apparent initial susceptibility, and the material should have a low saturation induction, preferably less than about 1.0 T.

Figure 3A:
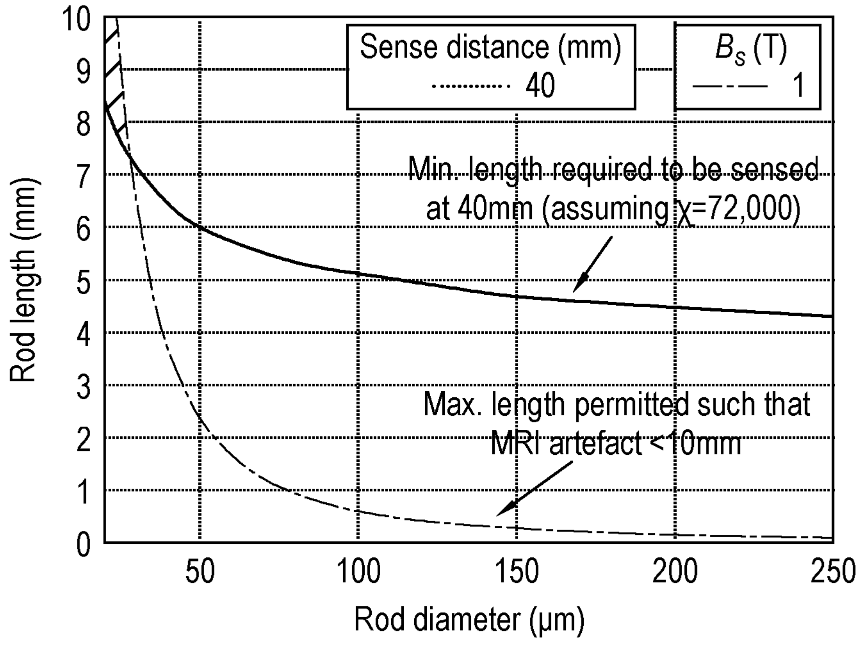
FIG. 3*a* is a graph of maximum wire length for a given maximum MRI artefact size and sensing performance at 40 mm distance vs both rod length and rod diameter for a ferromagnetic material of saturation induction $B_s$ of 1 T.

It has been surprisingly found that a thin long wire of ferromagnetic material could provide the required properties of an apparent susceptibility superior or equal to 1,000. FIG. 3*a* is a simulation confirming the feasibility of a straight wire that is detectable at useful range while showing a small MRI artefact. The dotted line shows, for each wire diameter, the minimum length required for it to be sensed at 40 mm, assuming the wire material has susceptibility $\chi$=72,000. The dot-dashed line shows, for each wire diameter, the maximum length permitted such that the MRI artefact of the wire has a diameter less than 10 mm, assuming the wire material has a saturation induction $B_s$ of 1 T. The hatched region in the upper-left corner of the graph corresponds to the wire dimensions that simultaneously are detectable at 40 mm or farther, and produce an MRI artefact of diameter 10 mm or smaller. This figure shows that the wire length must be much greater than the wire diameter to satisfy both of these conditions simultaneously.

Figure 3B:
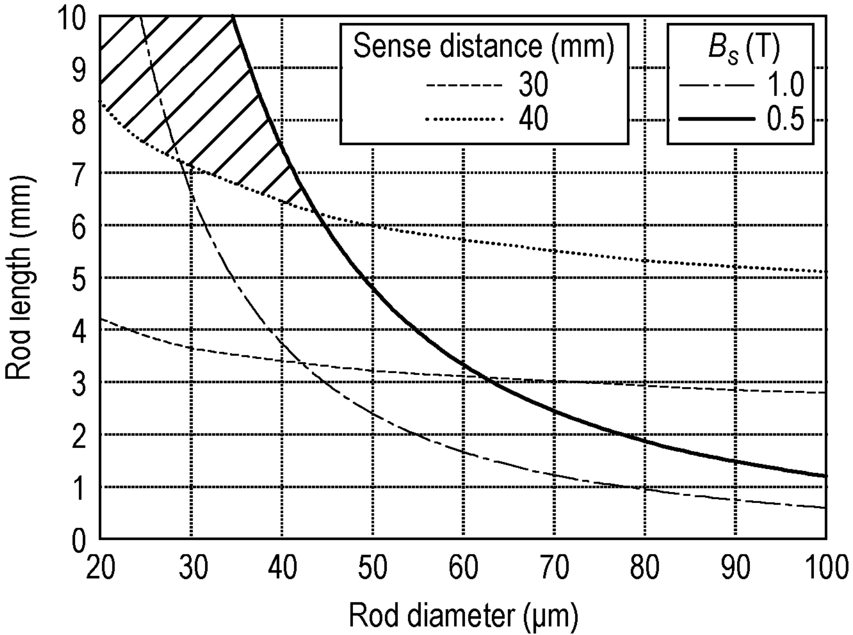
FIG. 3*b* is a graph of maximum wire length for a given maximum MRI artefact size and sensing performance at 30 mm or 40 mm distance vs both rod length and rod diameter for a ferromagnetic material with saturation induction $B_s$ of 0.5 T or 1.0 T.

FIG. 3*b* shows the same simulated data as FIG. 3*a*, but over a narrower range of wire diameters, and for more sense distances and saturation inductions. The dotted and dot-dashed lines have the same meaning as in FIG. 3*a*. The dashed and solid lines correspond to additional values of sense distance and saturation induction as indicated in the legend. This figure shows that a wide range of wire dimensions can be used if one accepts a lower sense distance (30 mm rather than 40 mm); or if the material has a lower saturation induction (0.5T rather than 1T).

A low saturation magnetization gives a small ferromagnetic dipole in the MRI scanner, and a high initial permeability means a small volume of material will give a large sense response on a probe such as magnetic susceptometry probes such as the one described in WO 2014/140566 A1, the contents of which are incorporated herein by reference.

| Change in marker characteristic | Effect on MRI artefact | Effect on susceptometry sensing response | Conclusion |
|---|---|---|---|
| Reduced volume of marker material | Reduces artefact (proportional to $V^{1/3}$) | Reduces sensing response (proportional to V) | Reducing volume reduces artefact size but reduces sensing response by a greater factor |
| Reduced material saturation induction ($B_s$) | Reduces artefact (proportional to $B^{1/3}$) | Minimal impact | Saturation induction is preferably minimised to reduce MRI artefact without affecting sensing |
| High initial permeability of marker material | No impact | Increases sensing response up to $\mu_r$ = ~1000 | Initial permeability is preferably at least 1000 for adequate sensing |
| Increased length to diameter ratio of marker material (i.e. increased apparent susceptibility) | No impact (if volume stays the same) | Increases sensing distance (proportional to apparent susceptibility $\chi_{app}$) | Length:diameter ratio should be maximised for increased sensing for a given volume of material (or same sensing with reduced volume) |

The sense response under a magnetic susceptometry probe field and the MRI artefact of a ferromagnetic material depend on different variables. It has been recognised that in a small oscillating field, such as that produced by Sentimag™, which is commercially available from Endomagnetics Ltd, UK, the sense performance depends almost exclusively on aspect ratio and volume, with a weaker dependence on the relative initial permeability, $\mu_{r,i}$ (the initial gradient of the B-$\mu_0$H curve). In contrast, the magnitude of magnetic field produced by the marker in an MRI machine, and hence the MRI artefact size, depends on the saturation induction $B_s$ and volume of material. This means that it is possible to produce the required small MRI artefact with a very thin piece of low-saturation-induction ferromagnetic material that can still be sensed at a satisfactory distance, as demonstrated in Table 1 below for a material with $\chi$=72,000 and $B_s$=0.5 T:

TABLE 1

| Wire ø (μm) | Wire length (mm) | Wire volume ($mm^3$) | Simulated MRI artefact ø (mm) | Simulated axial sensing distance (mm) |
|---|---|---|---|---|
| 685 | 1.6 | 0.590 | 40 | 30 |
| 198 | 2.5 | 0.077 | 20 | 30 |
| 122 | 2.7 | 0.032 | 15 | 30 |
| 62 | 3.1 | 0.009 | 10 | 30 |

A marker having a large aspect ratio, preferably having a length to diameter ratio of at least 50, more preferably at least 60, especially at least 100, and more especially at least about 500, with a low total volume, such as one having a length of at least 3 mm, preferably being at least 6 mm long with a diameter less than 100 μm, preferably having a diameter equal to or less than 50 μm, especially equal to or less than 30 μm piece of low-saturation-induction ferromagnetic material was found to be sensed adequately while producing a low MRI artefact.

This is demonstrated in FIGS. 3*a* and 3*b* of the accompanying drawings, which demonstrate MRI performance depending upon the rod length and diameter. For a given $B_s$, anything below the contour gives an acceptable artefact Example 2: Study into Preferred Materials for a Magnetic Marker According to the Disclosure The marker described in Example 1 was further investigated to allow selection of the preferred magnetic materials that would produce the required high initial relative permeability $\mu_{r,i}$>1000, be formable into very thin strips or wire to allow the large aspect ratio but low volume to be configured, and having a low saturation induction $B_s$, ideally having a low $B_s$ of less than 1 T.

Preferred materials that possess the required characteristics were found to be particular metals, amorphous metals and ceramic ferrites, preferably cobalt-based amorphous metals such as those sold under the trade names Yshield MCE61™, Metglas 2705M™ and Metglas 2714A™; Manganese-Zinc ceramic ferrites such as those sold under the trade names Fair-Rites 31™, 76™ and 78™; Nickel-iron-based soft ferromagnetic alloys such as those sold under the trade names Mu-metal, Permalloy 80, Permalloy C, Permalloy and Supermalloy; Nickel-Zinc ceramic ferrites such as those sold under the trade names Fair-Rites 15™, 20™, and 43™; and more preferably Cobalt-based amorphous metals such as Yshield™ and Metglas 2714A™.

Ceramics, although having a low saturation induction, are less easy to form into wire or flat wire and therefore are less suitable for a marker according to the disclosure.

Figure 4:
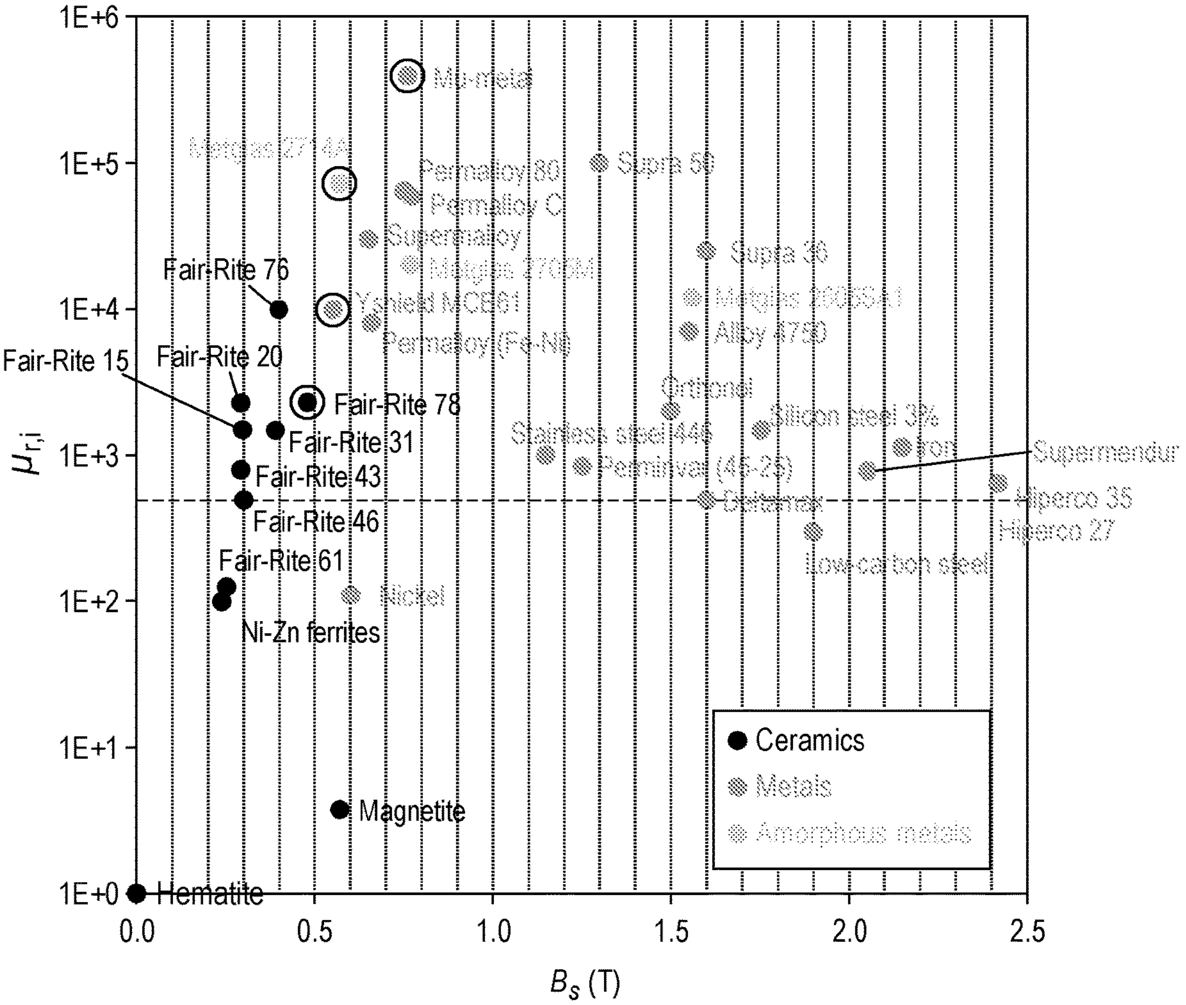
FIG. 4 is a graph of saturation induction ($B_s$) against initial relative magnetic permeability ($\mu_{r,i}$) for various ceramics, metals and amorphous metals.

FIG. 4 is a plot of saturation induction against initial relative permeability for a wide variety of different materials. The materials which may form suitable markers are contained in the top left hand region of the graph, demonstrating low saturation induction and high relative initial permeability.

Example 3: Investigation into Optimized Design for a Magnetic Marker According to the Disclosure The thin long wire marker discussed in relation to Examples 1 and 2 provides the required initial relative permeability $\mu_{r,i}$>1000, preferably >10,000, large aspect ratio but low volume and has a low saturation induction $B_s$. However, this type of marker has a high anisotropy ratio, demonstrating a strong sense response only in the direction of its axis.

From a practical perspective, during surgery to detect the marker using a magnetic probe as described in WO2014/

013235, high anisotropy is undesirable: the magnetic signal at a constant distance will vary depending on the orientation of the marker relative to the probe and make the marker appear to be closer when approaching from some orientations and further away from others. Minimising the anisotropy for the implanted marker improves the surgeons' ability to localise the marker by making it more intuitive and increases the surgeons' ability to remove a safe margin of tissue around a lesion. An anisotropy ratio of 1 is the ideal, giving a uniform response from any direction. However, in practice this is challenging to achieve within the geometric constraints of delivery through a small needle. An anisotropy ratio of less than 7 (i.e. between 1 and 7), preferably less than 5 and more preferably less than 3 is desirable. Because the magnetic sense response depends strongly on distance (under certain conditions, approximately in inverse proportion to its sixth power), conversely the calculated distance depends relatively weakly on the magnetic sense response. Therefore an anisotropy ratio of less than 2 is close enough to the ideal for practical use, a ratio of 5 may not be distinguishable in practice from isotropic, and a ratio of 7 may provide adequate uniformity.

Two ways have been identified to increase the axial sensing and increase isotropy of magnetic susceptibility. It was also desirable to provide a marker that does not need to be unpacked at the injection site since deployable concepts need to have a consistent unpacking mechanism to allow for accurate placement and a full unpacking to give the necessary sensitivity and isotropy. Thus, having a marker that does not need to be unpacked at the injection site would also provide a significant improvement over the prior art. To achieve this, a marker may comprise a multitude of small ferromagnetic rods using the wire of Example 1 encapsulated within a single cylinder where all axes would be covered. However, this type of marker still faced several challenges in terms of detection sensibility (as short rods are expected to have a low axial susceptibility and some destructive interactive effects), MRI artefact (as the complexity of the magnetic dipoles would be at the utmost complexity to estimate), safety and regulation and manufacturing process for encapsulation of the rods and consistency.

Thus, further configurations were investigated for optimized markers according to the disclosure. For a given artefact size, it has been determined that there is a constraint on the maximum volume of magnetic material you can employ for use in a marker. The use of a material having a low saturation induction $B_s$ will enable more material to be used. The wire's diameter will dictate the total length of wire available and its relative permeability and the aspect ratio of the wire can then be used to calculate the sense response.

The key variables have been identified that can be modified to improve the design of marker as the total wire volume and the wire length as the strongest dependence on the artefact diameter is the diameter of the wire and therefore the latter does not offer much variability. If a design consists of a wire diameter D, the permitted length of wire L is:

$$L = D^3_{artefact,y} \cdot \frac{1}{D^2_{wire}} \cdot \frac{B_{crit}}{B_s}$$

Initially, an arrangement containing multiple rods of the thin wire arranged in different orientations was considered to enhance the anisotropy of the marker. It has been unexpectedly found that neighbouring rods can have positive or negative interactions on the total dipole moment, as demonstrated in FIGS. 5*a*, 5*b* and 5*c* of the accompanying drawings.

Figure 5A:
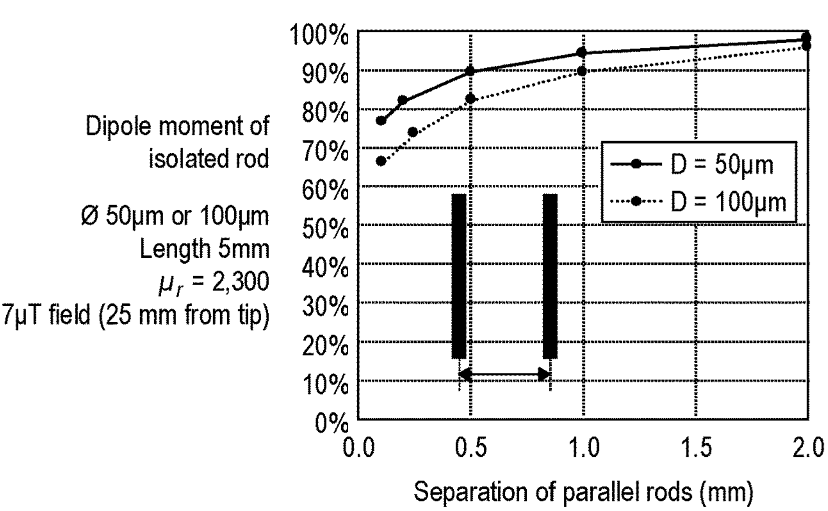
FIG. 5*a* is a graph illustrating the magnetic dipole moment of one of two parallel spaced apart rods having a diameter of 50 μm and 100 μm with a length of 5 mm and relative permeability of 2300 when exposed to a weak magnetic field (of approximately of 7 T in the present case)
Figure 5B:
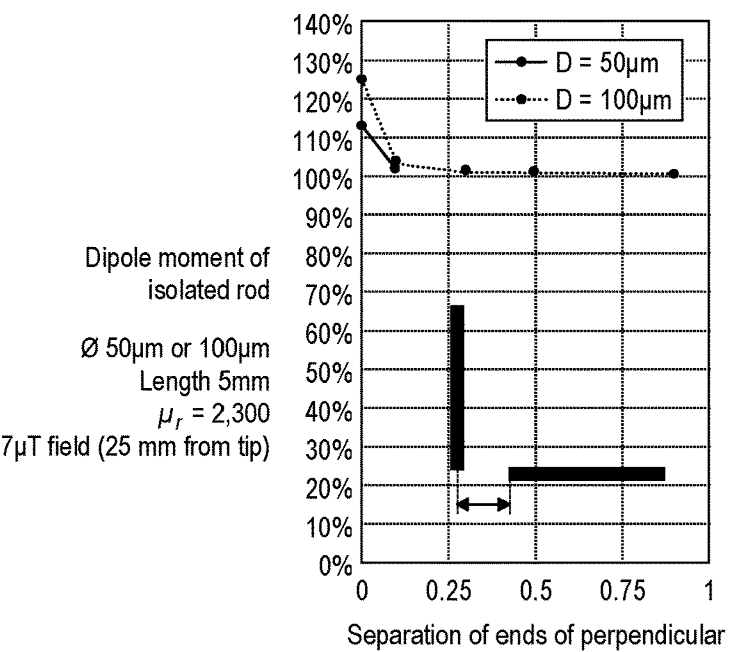
FIG. 5*b* is a graph illustrating the dipole moment of one of two mutually perpendicular spaced apart rods having a diameter of 50 μm and 100 μm with a length of 5 mm and relative permeability of 2300 when exposed to a weak magnetic field (of approximately of 7 T in the present case)
Figure 5C:
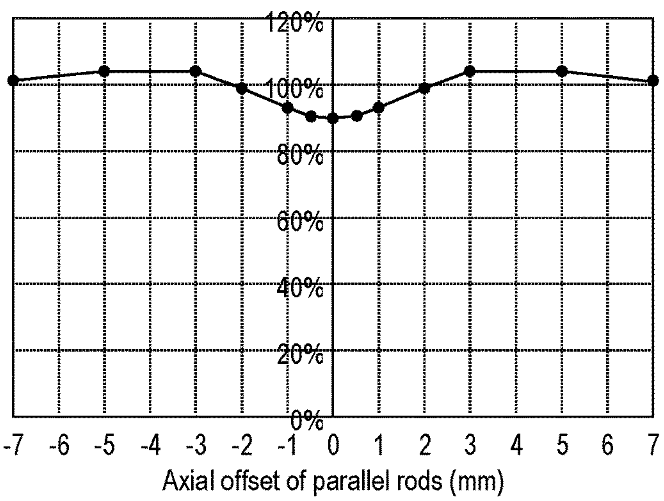
FIG. 5*c* is a graph illustrating the dipole moment of one of two axially offset parallel spaced apart rods having a diameter of 50 μm with a length of 5 mm and permeability of 2300 when exposed to a weak magnetic field (of approximately of 7 T in the present case)

FIG. 5*a* shows that parallel rods placed 0.5 mm apart from each other decrease the dipole moment by 5% for 50 m diameter rods and by 10% for 100 m diameter rods. On the contrary and as seen on FIG. 5*b*, two identical rods placed perpendicularly and where the ends are separated by a rod diameter length will increase the total dipole moment by 5%. Additionally, perpendicular rods show a smaller decrease of their dipole moments if offset axially as seen in FIG. 5*c*.

Based on these findings, marker configurations with closely spaced parallel rods were excluded as markers of the disclosure. However, satisfactory markers forming embodiments of the disclosure were configurations where it is possible to offset the placement of these parallel rods, as shown in FIG. 5*c*. Further embodiments are shapes where perpendicular rods could be placed end on end.

Preferred spacings for the rods are at least one diameter space apart.

The rods provided in the required configuration may be encapsulated in a cylindrical housing as is known in the art. For example, the marker may be packaged within other materials to ensure they are biocompatible to prevent a reaction with body tissue, and robust or a coating may be applied to the marker. The marker may be encased in a tube, for example made from Nitinol, titanium, stainless steel or other biocompatible alloys, the material preferably being non-magnetic and having a relatively low conductivity. Suitable coating materials include a polymer coating, such as FEP, Parylene, PTFE, ETFE, PE, PET, PVC or silicone or an epoxy based encapsulant.

Given the difficulty to assess magnetic dipole moments in a complex structure, a methodology has been developed to establish how different shapes behave and interact together. The findings are summarised in FIG. 6.

It was concluded that larger aspect ratio designs, either longer rods or larger rings, will produce a design with a much better sense performance to MRI artefact. In this respect, per unit volume, 5 mm long rods were found to be around eight times better than 1 mm long ones and per unit volume, a ring was found to be better than two perpendicular rods. Ring or coil-based designs were also determined to be better than two perpendicular rods to produce sense response in two directions.

In this respect, referring to FIG. 6 of the accompanying drawings, the quantity $m_z/V$ indicates how much sensing response the marker produces per unit volume. Although the 5 mm straight rod produces a stronger response per unit volume than the ring ($m_z/V$ of 54 for the rod vs 42 for the ring), the rod produces a magnetic response only along its axis, while the ring does so in the two dimensions covered by its plane. Therefore the correct figure of merit for the ring is 2×42=84, i.e. ~50% better than the rod.

FIG. 7 of the accompanying drawings illustrates the configuration of a number of markers according to embodiments of the present disclosure that were found to produce the required low MRI artefact with good sense response in multiple directions. FIG. 7 provides the sense distance at 200 mA for an artefact diameter of diameter 10 mm. The material parameters are: $\mu_r$=72,000, $B_s$=0.55 T and the diameter of the wire is 30 μm, with a maximum total length of 21 mm.

This figure also highlights the preferred embodiments for this disclosure which are the helix shape, rings and offset parallel or perpendicular rod arrangements. These provide the best performance per volume of material used.

Example 4: Further Investigations in Relation to Helical Coil Marker According to Examples of the Present Disclosure Given the ease of manufacture of a helix shape, the optimisation of this shape was further investigated as a preferred marker according to the disclosure.

Figure 8A:
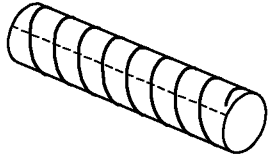
FIG. 8*a* is a schematic perspective view of a marker according to an embodiment of the present disclosure.
Figure 8B:
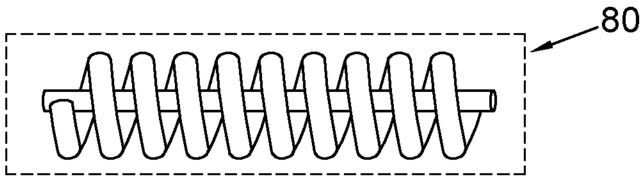
FIG. 8*b* is a schematic side view of the marker of FIG. 8*a*, with an optional marker housing shown in dotted lines.
Figure 9A:
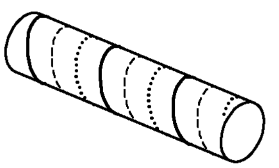
FIG. 9*a* is a schematic perspective view of a marker according to another embodiment of the present disclosure.
Figure 9B:
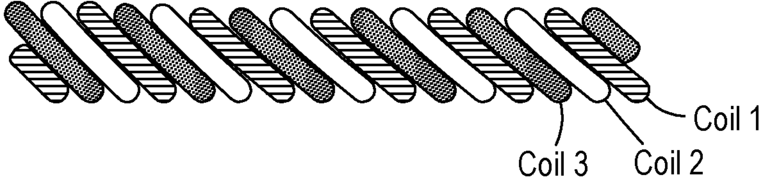
FIG. 9*b* is a schematic side view of the marker of FIG. 9*a;*

It was demonstrated that two types of different helical designs produce an acceptable sense response, both in terms of minimum sense distance and isotopy. As shown in FIGS. 8*a* to 9*b* respectively, these are (i) single helix combined with one longitudinal wire aligned parallel to the axis core (FIGS. 8*a* and 8*b*) and (ii) a multiple helix, consisting of a double or triple helix (FIGS. 9*a* and 9*b*). In FIGS. 8*a* and 8*b*, the longitudinal wire is aligned parallel and co-axial with the axis core. In an alternative arrangement the longitudinal wire is located at a side of the helix rather than co-axial with the axis core.

A marker with a single helix design gets its transverse response from its helical coil, and the majority of its axial response from its axial rod, while a marker with the triple helix design uses a larger pitch to get both its transverse and axial response from its helical coil (the larger pitch means the coils point more towards the axial direction). In the context of triple and other multiple hexices, the term “pitch” as used herein means the pitch of each constituent individual coil of the multiple helix, unless the clear context implies otherwise.

The sense distance has been predicted using a combination of standard physics simulation software (COMSOL), custom computer models and experimentation, for one or several axial rods used and for two diameters, as shown in Table 2 below.

TABLE 2

| Length of axial rod | Ø15 μm Co—Fe amorphous metal predicted sense distance (mm) | | | | Ø30 μm Co—Fe amorphous metal predicted sense distance (mm) | |
|---|---|---|---|---|---|---|
| (mm) | 1 rod | 2 rods | 3 rods | 4 rods | 1 rod | 2 rods |
| 4 | 27 | 31 | 34 | 35 | 30 | 35 |
| 5 | 30 | 34 | 37 | 38 | 33 | 38 |
| 6 | 32 | 36 | 39 | 41 | 36 | 40 |
| 7 | 33 | 38 | 41 | 43 | 38 | 43 |
| 8 | — | — | — | — | 40 | — |
| 9 | — | — | — | — | 42 | — |

According to the present disclosure, it is desirable to minimise the amount of material used to minimise the MRI artefact and, by combining this with the results of the simulation, it can be concluded that it is desirable to use a smaller diameter and one longer rod rather than two shorter ones.

For a single helix design with a longitudinal wire aligned parallel to the axis of the core (FIGS. 8*a* and 8*b*), it has been determined that it is necessary to use the thinnest wire possible (see Example 1 above) with the maximum length of wire possible. One should also maximise the diameter of the coil to provide a stronger transverse sense response for the same volume of material, as illustrated in FIG. 6. FIG. 8*b* shows an optional housing or tube 80 in dotted lines located around the helical coil. The marker may be encased in a tube, for example made from Nitinol, titanium, stainless steel or other biocompatible alloys, the material preferably being non-magnetic and having a relatively low conductivity. Suitable coating materials include a polymer coating, such as FEP, Parylene, PTFE, ETFE, PE, PET, PVC or silicone or an epoxy based encapsulant.

Figures 10A, 10B, 10C:
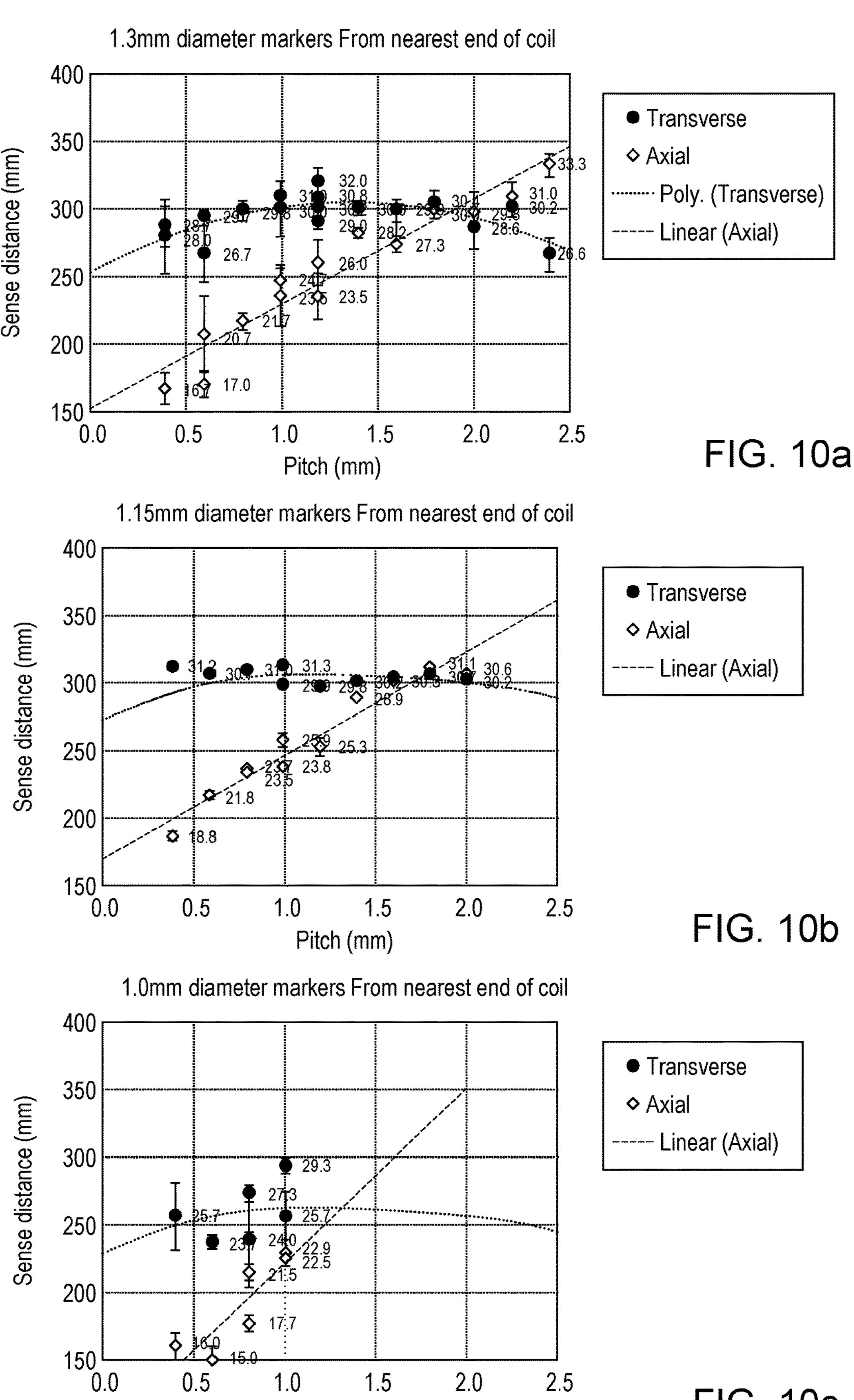
FIGS. 10*a* to 10*c* are graphs of sense distance (mm) vs pitch (mm) for 1.3 mm diameter markers, 1.15 mm diameter markers and 1.0 mm diameter markers respectively.

The graph of pitch against transverse sensing distance surprisingly does not show a sharp peak around the optimal value, and the pitch must be balanced with the axial sensing increase to reach a sweet spot. FIGS. 10*a* to 10*c* show that the pitch that maximizes transverse sense performance approximately equals the helix diameter—this is the optimal pitch for the single helix design where helical coil must only produce the transverse sense response and the axial component comes from the axial wire. While the pitch that produces isotropic sense performance approximately equals 1.6×the helix diameter—this pitch is useful for the multiple helix designs that exclude the axial wire, and so both the axial and transverse sense response must be produced by the helical coil. FIGS. 10*a* to 10*c* illustrate the sense distance (mm) against pitch (mm) for 1 mm diameter markers, 1.15 mm diameter markers and 1.3 mm diameter markers respectively.

The other design option of having multiple helices to avoid the need for the axial rod was investigated further. Table 3 below shows that with the same total length of wire, the total number of turns per helix increases between one helix with a rod and a double helix or triple helix without rod.

TABLE 3

| Marker Size OD × L (mm) | No. of helices | Pitch (mm) | Axial wire (mm) | Turns per helix | Total number of turns | Total length of wire (mm) | Length of marker (mm) |
|---|---|---|---|---|---|---|---|
| 1.15 × 8.0 | Single | 1.0 | 8 | 8.0 | 8.0 | 38.0 | 8.0 |
| 1.15 × 8.0 | Double | 1.7 | n/a | 4.8 | 9.6 | 38.0 | 8.0 |
| 1.15 × 8.0 | Triple | 2.4 | n/a | 2.8 | 8.4 | 38.0 | 8.0 |

To keep the same marker length and diameter, the double helix and triple helix have higher pitch which was expected to give better axial detection but surprisingly and as shown in Table 4 below, the transverse detection was only slightly affected and even more surprisingly it has been found that the transverse detection increased. A major unexpected finding was also the non-destructive effect on the susceptibility of having helices interlaced in close proximity with one another, without touching.

As a conclusion, it has been found that for a given amount of material and marker length, a single helix will present a short pitch and may require combination with a ferromagnetic rod. Alternatively, a double or triple helix incorporated into a marker with the same amount of material for the same length will require the helices to be stretched so that the pitch increases and this helps move the coils in a more axial direction but surprisingly does not decrease the transverse detection.

If a stronger sense performance is required in a more compact shape, a higher order helix may be used to provide more coils per unit length. However, if too many coils are closely packed together, (spacing less than 1×the diameter of the coil), they will start to destructively interact.

Marker size for all cases in Table 4 was diameter of 1.15 mm and length of 8.0 mm.

TABLE 4

| No. of helices | Pitch (mm) | Axial wire (mm) | Turns per helix | Total number of turns | Total length of wire (mm) | Length of marker (mm) | Transverse sense distance (mm) | Axial sense distance |
|---|---|---|---|---|---|---|---|---|
| Single | 1.0 | 8 | 8.0 | 8.0 | 38 | 8.0 | 30 | 34 |
| Double | 2.0 | n/a | 4.0 | 8.0 | 34 | 8.0 | 30 | 31 |
| Triple | 3.0 | n/a | 2.7 | 8.4 | 38 | 8.0 | 30 | 35 |
| Triple | 2.6 | n/a | 3.1 | 9.2 | 41 | 8.0 | 31 | 34 |
| Triple | 2.0 | n/a | 4.0 | 12.0 | 51 | 8.0 | 33 | 33 |

As noted from Table 4 above, decreasing the pitch and increasing the number of turns will increase the transverse sense performance but will decrease the axial sense performance. It will also increase the total length of wire used which will increase the MRI artefact size. Increasing the pitch and decreasing the number of turns will decrease the transverse sense performance but will increase the axial sense performance. It will also decrease the total length of wire used which will decrease the MRI artefact size. There is an optimum pitch to produce an isotropic sense performance for each type of multi helices marker (e.g. for triple helices it is ~2.0 mm pitch for a 1.15 mm diameter marker using 15 um Co—Fe amorphous metal wire.)

Example 5: Investigation into Alternative Ferromagnetic Materials for Markers According to the Present Disclosure The markers hereinbefore disclosed all use thin wire as described in relation to Example 1 above to produce an optimized design of marker. However, preferred magnetic materials that would produce the required high initial relative permeability $\mu_{r,i}$>1000, preferably >10,000, and have a low saturation induction $B_s$ may also be formable into strips, flat wires with an oblong section for providing markers according to the disclosure.

For example, Table 5 below illustrates iron metal alloys having $\mu_{r,i}\geq$15,000 that meet the requirements for a marker according to the disclosure and may be provided in rolled sheet form prior to being cut into wires or strips.

TABLE 5

| Material (and type) | Form | $B_s$ (T) | $\mu_r$ | Curie temp (° C.) | Material size (μm) | Performance indicator** |
|---|---|---|---|---|---|---|
| Co—Fe amorphous metal (Co—Fe amorphous metal) | Wire | 0.6 | 15,000 | 300 | 30 | 1 |
| Metglas 2714A (Cobalt-based amorphous metal) | Sheet | 0.57 | 72,000 | 225 | 15 | 4.2 |
| ULTRAPERM (Ni—Fe metal alloy) | Sheet | 0.74 | 300,000 | 360 | 20 | 1.8 |
| Supermalloy (Ni—Fe metal alloy) | Sheet | 0.65 | 30,000 | 460 | (20) | (2.1) |

**Indicator of the amount of material available for a given artefact size. More material should give a stronger signal response.

Marker designs can be created from these thin sheets using known manufacturing techniques, such as etching or laser cutting. These manufacturing techniques would aim to create wires that may or may not result in a flattened shape. In the case of flattened wire, the diameter described in other sections of this application essentially corresponds to the average radial length of the wire.

It is readily apparent from the above description that the implantable markers according to the disclosure provide small ferromagnetic markers with good isotropy of magnetic susceptibility, sense distance and showing a small MRI artefact.

Example 6: Use of Markers According to the Disclosure in the Monitoring and Treatment of Breast Cancer The markers according to the present disclosure are particularly suitable for the monitoring and treatment of breast cancer, enabling tracking of the size of the tumour during preliminary neoadjuvant therapy with the aim of shrinking the size of the tumour below 2 cm long or to at least a size that is sufficiently small compared to the overall (BCS).

Patients that present abreast cancer tumour of more than 2 cm but less than 5 cm and which has not spread further than the lymphatic nodes in close proximity (often categorised as "Stage 2" breast cancer) can be offered BCS but this generally requires neoadjuvant therapy to shrink the tumour to around 2 cm or less. In parallel with this, the healthcare professional will also need to assess the exact nature of the tumour, typically requiring a biopsy to be performed to sample some of the tumoral tissue.

Figure 20:
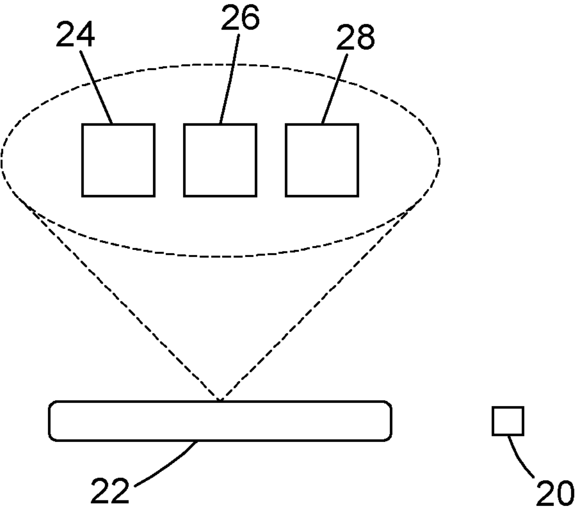
FIG. 20 shows a detection system for locating a marker according to the present disclosure.

A marker according to the present disclosure can be placed in the cavity created by the tissue sampling in order to locate the tumour using a magnetic susceptometry probe, such as the probe described in WO 2014/140566 A1. This enables the tumour to be located during future assessments of tumour progression and/or for ablation of the tumour. A susceptometry detection system for locating a marker is shown in FIG. 20, where a marker 20 according to the present disclosure is shown, along with a magnetic susceptibility probe 22, the probe 22 including a drive coil 24 arranged to excite the marker with an alternating magnetic field, and a detector 24 arranged to receive the signal from the sense coil. A magnetic field generator 28 is arranged to drive an alternating magnetic field through the drive coil 24, and the detector 24 is arranged to detect one or more harmonics of the drive frequency in the received signal.

The marker of the disclosure also enables the tumour response to adjuvant therapy to be tracked by periodic examination, for example under MRI, due to the size of the artefact created under MRI field by the marker being kept to a minimum, ideally not more than 2 cm long. In this respect, the marker should not interfere with the assessment of tumour size while it is too big for BCS (essentially around 2 cm but possibly more).

Thus, the markers of the disclosure are particularly suitable for the protocol commonly pursued by healthcare professionals when tracking breast cancer progression under MRI due to their low induction saturation and low mass per volume which allows a significant reduction in the size of the MRI artefact. Once the tumour has shrunk to a size that allows BCS, the healthcare professional is able to locate the tumour by means of the marker. The markers can be detected by a magnetic susceptometry probe that is positioned at least 3 cm, up to 5 cm, away thereby enabling a tumour which may be a few centimetres below the surface of the skin to be located. This enables the healthcare professional to determine the best path to access and remove the tumour by ablation prior to incision of the tissue.

Figure 11A:
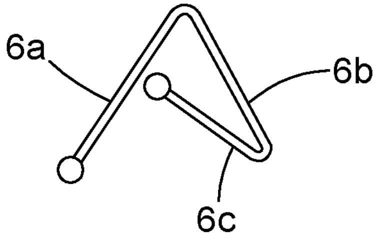
FIGS. 11 to 19 show further various possible marker configurations according to the present disclosure.
Figure 11B:
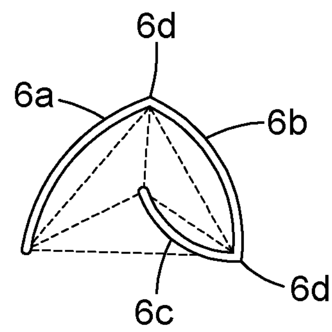
Figure 19:
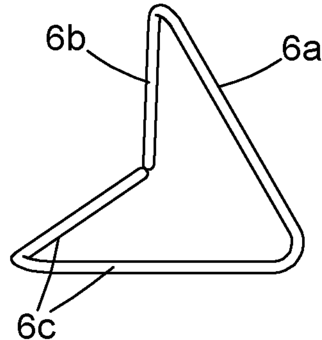

In FIGS. 11*a* and 11*b*, and 19, the marker 6 comprises a length of magnetic marker material bent to describe three or four edges 6*a*, 6*b*, 6*c* of a tetrahedron. By so doing, the harmonic signal response of the marker is more uniform from any given direction of sensing. In a further aspect, the radii of the bends 6*d* may be configured, e.g. by making them larger, to allow the marker to be packed into an outer tube more easily prior to deployment.

Figure 12:
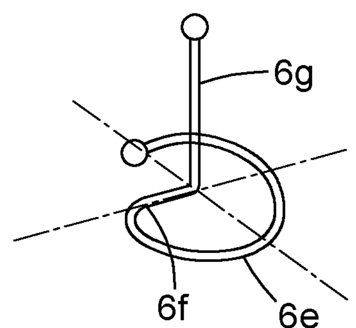

In FIG. 12, the marker comprises a length of magnetic marker material bent into a portion of a circle 6*e*, with one end 6*f* bent radially towards the centre and then bent substantially at 90° out of the plane of the circle 6*e* to form a portion 6*g* along or parallel to the axis of the circle.

Figure 13:
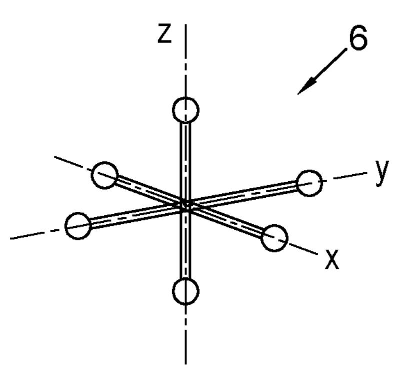

In FIG. 13, the marker 6 comprises lengths of magnetic marker material arranged along three orthogonal axes x, y and z to form the shape of a 'jack' (also known as a jackstone or knucklebone).

Figure 14A:
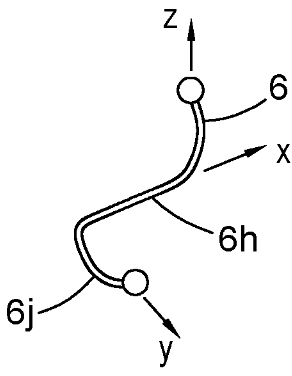
Figure 14B:
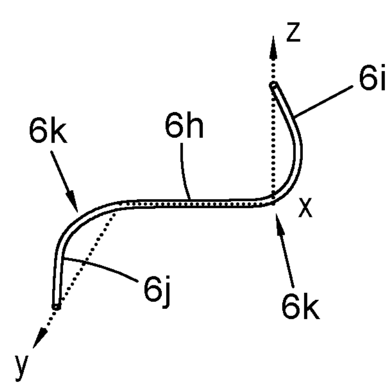

In FIGS. 14*a* and 14*b*, the marker comprises a length of magnetic marker material with a straight central section 6*h* and two further sections 6*i*, 6*j*, one at each end bent orthogonally from each other and from the central section. In a further aspect, the radii of the bends 6*k* may be larger to allow the marker to be inserted into an outer tube more easily.

Figure 15:
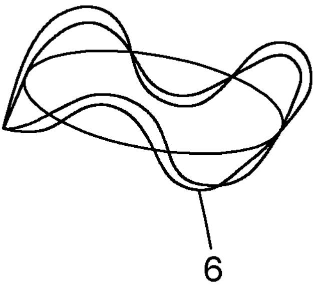

In FIG. 15 the marker 6 comprises a length of magnetic marker material in the shape of a circular standing wave, i.e. formed into a uniform wave shape and then bent round to join the ends and form a circle in plan view.

Figure 16:
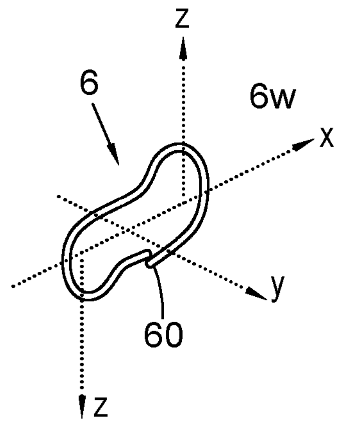

In FIG. 16, the marker comprises an elliptical or oval shaped length of magnetic marker material 6*n* with the wire ends 6*o* joined or close to one another but not joined. Two portions of the ellipse or oval at the ends of its longer axis are bent to approximately 90° of the plane of the ellipse. The bent portions comprise approximately one quarter to one third of the area of the ellipse or oval.

Figure 17:
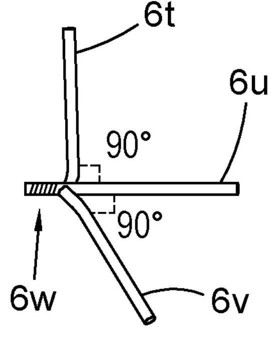

In FIG. 17, the marker comprises three lengths of magnetic marker material 6*t*,6*u*,6*v* arranged orthogonally to each other to form substantially an orthogonal tripod or the vertex of a cuboid. The three lengths are joined with a joining section 6*w* that allows the lengths to he parallel to each other prior to deployment and then redeploy to form an orthogonal tripod.

Figure 18A:
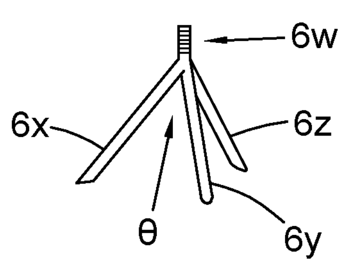
Figure 18B:
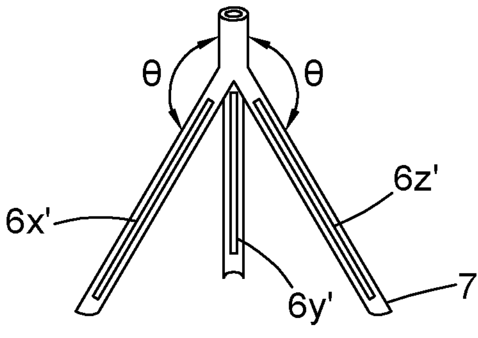

In FIGS. 18*a* and 18*b*, the marker comprises three lengths of magnetic marker material 6*x*,6*y*,6*z* arranged to form a tripod with a non-orthogonal angle between the legs of the tripod. The three lengths are joined with a joining section 6*w* that allows the lengths to be parallel to each other prior to deployment and then redeploy to form the tripod.

In one embodiment, the magnetic marker may comprise a wire made of ferromagnetic material in the form of a helical coil with the following properties:

| Criteria | Magnetic marker |
|---|---|
| Wire length | 36 mm |
| Wire diameter | 0.015 mm |
| Total wire length to diameter ratio | 2400 |
| Volume of ferromagnetic material | $6.4 \times 10^{-12}$ m$^3$ |
| Total marker length excluding heat shrink and capsule | 5 mm |
| Pitch | 1.6 mm |
| Number of coils | 3 coils |
| Core diameter | 1.2 mm |
| Core length | 5 mm |
| Core volume | $5.65 \times 10^{-9}$ m$^3$ |
| Volume of diamagnetic/ferromagnetic | 883 |

Preferably the angle between the legs is chosen such that the harmonic magnetic response is as uniform as possible from any direction. The tripod is uniform with three equally spaced legs.

Whilst the marker of the present disclosure have been described and illustrated with reference to particular embodiments, it will be appreciated by those of ordinary skill in the art that the markers lend themselves to many different variations not specifically illustrated herein.

Where in the foregoing description, integers or elements are mentioned which have known, obvious or foreseeable equivalents, then such equivalents are herein incorporated as if individually set forth. Reference should be made to the claims for determining the true scope of the present disclosure, which should be construed so as to encompass any such equivalents. It will also be appreciated by the reader that integers or features of the disclosure that are described as preferable, advantageous, convenient or the like are optional and do not limit the scope of the independent claims. Moreover, it is to be understood that such optional integers or features, whilst of possible benefit in some embodiments of the disclosure, may not be desirable, and may therefore be absent, in other embodiments.

The invention claimed is:

1. An implantable marker for imaging and surgical guidance, the marker comprising one or more pieces of a ferromagnetic material having a total length to diameter ratio of at least about 500, and a total volume of less than about $1\times10^{-11}$ m$^3$, wherein the one or more pieces of ferromagnetic material has a high initial relative permeability ($\mu_{r,i}$)>about 1000, wherein the marker has a magnetic anisotropy ratio of less than about 7, preferably less than about 5.

2. The marker as claimed in claim 1, wherein the total length to diameter ratio of the one or more pieces of ferromagnetic material is at least about 650, preferably at least about 750 or at least about 1000 or at least about 2000.

3. The marker as claimed in claim 1, wherein the total volume of the one or more pieces of ferromagnetic material is less than about $6\times10^{-12}$ m$^3$.

4. The marker as claimed in claim 1, wherein the one or more pieces of ferromagnetic material has a low saturation induction of equal to or less than about 1 T.

5. The marker as claimed in claim 1, wherein the one or more pieces of ferromagnetic material is a wire or strip.

6. The marker as claimed in claim 1, wherein the marker comprises a wire or strip of ferromagnetic material having a length of at least about 10 mm, optionally at least about 20 mm.

7. The marker as claimed in claim 1, wherein the marker comprises a wire of ferromagnetic material with a diameter of less than about 100 μm, optionally less than about 30 μm.

8. The marker as claimed in claim 1, wherein the ferromagnetic material is selected from cobalt-based amorphous metals; manganese-zinc ferrites; nickel-iron-based soft ferromagnetic alloys; and nickel-zinc ferrites; and more preferably cobalt-based amorphous metals.

9. A marker as claimed in claim 1, wherein the one or more pieces of ferromagnetic material comprise one or more wires or strips extending in different directions in the same or different planes.

10. The marker as claimed in claim 1, wherein the one or more pieces of ferromagnetic material comprise one or more helical coils.

11. The marker as claimed in claim 10, wherein the one or more pieces of ferromagnetic material comprise one or more straight rods extending through the one or more helical coils.

12. The marker as claimed in claim 10, wherein the pitch of the or each helical coil is about 1.0-1.5 the diameter of the coil.

13. The marker as claimed in claim 1, wherein the one or more pieces of ferromagnetic material comprise multiple spaced apart rings, optionally wherein the one or more pieces of ferromagnetic material comprise one or more straight rods extending through the multiple spaced apart rings.

14. The marker as claimed in claim 1, wherein the one or more pieces of ferromagnetic material comprise a single helical coil combined with a straight wire which is aligned parallel to the helical coil axis.

15. The marker as claimed in claim 1, wherein the one or more pieces of ferromagnetic material comprise multiple helical coils, optionally forming a double or triple helix.

16. A detection system for locating an implantable marker, the system comprising:

an implantable marker as claimed in claim 1;

at least one drive coil arranged to excite the marker with an alternating magnetic field and at least one sense coil arranged to detect a signal received from the excited marker;

a magnetic field generator arranged to drive an alternating magnetic field through the at least drive coil; and at least one detector arranged to receive the signal from the sense coil and detect one or more harmonics of the drive frequency in the received signal.

17. The marker as claimed in claim 1, wherein the high initial relative permeability and the magnetic anisotropy ratio are selected to increase detection sensibility of the marker by a handheld susceptibility probe.

18. The marker as claimed in claim 17, wherein the increase in detection sensibility corresponds to an increase in detection distance between the marker and the probe.

19. An implantable marker for imaging and surgical guidance, the marker comprising one or more pieces of a ferromagnetic material having a total length to diameter ratio of at least 50, and a total volume of less than $1\times10^{-10}$ $m^3$; wherein the one or more pieces of ferromagnetic material comprise one or more helical coils, wherein the one or more pieces of ferromagnetic material have a high initial relative permeability ($\mu_{r,i}$)>about 1000, wherein the marker has a magnetic anisotropy ratio of less than about 7, preferably less than about 5.

20. The marker as claimed in claim 19, wherein the total volume of the one or more pieces of ferromagnetic material is less than about $1\times10^{-11}$ $m^3$.

21. The marker as claimed in claim 19, wherein the total length to diameter ratio of the one or more pieces of ferromagnetic material is at least about 500.

22. The marker as claimed in claim 19, wherein the high initial relative permeability and the magnetic anisotropy ratio are selected to increase detection sensibility of the marker by a handheld susceptibility probe.

23. An implantable marker for imaging and surgical guidance and being configured to produce a Magnetic Resonance Imaging (MRI) artefact of less than 2 cm diameter when imaged in an MRI scanner, the marker comprising one or more pieces of a ferromagnetic material having a total volume of less than about $1\times10^{-10}$ $m^3$ and a high initial relative permeability ($\mu_{r,i}$)>about 1000, wherein the marker has a magnetic anisotropy ratio of less than about 7, preferably less than about 5.

24. The marker as claimed in claim 23, wherein the MRI scanner has a field strength of 1.5T or 3T.

25. The marker as claimed in claim 23, wherein the high initial relative permeability and the magnetic anisotropy ratio are selected to increase detection sensibility of the marker by a handheld susceptibility probe.

* * * * *